(12) United States Patent
Chen et al.

(10) Patent No.: US 11,517,728 B2
(45) Date of Patent: Dec. 6, 2022

(54) SURGERY DRAINAGE TUBE

(71) Applicant: WUXI SECOND PEOPLE'S HOSPITAL, Wuxi (CN)

(72) Inventors: Yigang Chen, Wuxi (CN); Jiazeng Xia, Wuxi (CN)

(73) Assignee: WUXI SECOND PEOPLE'S HOSPITAL, Wuxi (CN)

( * ) Notice: Subject to any disclaimer, the term of this patent is extended or adjusted under 35 U.S.C. 154(b) by 0 days.

(21) Appl. No.: 17/408,517

(22) Filed: Aug. 23, 2021

(65) Prior Publication Data
US 2022/0062600 A1    Mar. 3, 2022

(30) Foreign Application Priority Data
Aug. 25, 2020  (CN) .......................... 2020108618027

(51) Int. Cl.
*A61M 27/00*    (2006.01)

(52) U.S. Cl.
CPC .................................. *A61M 27/00* (2013.01)

(58) Field of Classification Search
CPC ...... A61M 25/02; A61M 25/01; A61M 25/00; A61M 2025/0286
See application file for complete search history.

(56) References Cited

U.S. PATENT DOCUMENTS

2008/0300548 A1* 12/2008 Massengale .......... A61M 25/02
606/108

* cited by examiner

*Primary Examiner* — Nicholas J. Weiss
*Assistant Examiner* — Gabriella E Burnette

(57) ABSTRACT

The present disclosure provides a detachable surgery drainage tube capable of being sutured and fixed, relates to a technical field of surgery drainage tubes, including a tube body, a suture line, and a first limiting component. The tube body is hollow. The suture line has a length, and is configured to act on a part to be drained. The first limiting component is an annular structure, and a structure of the first limiting component is easy to be cut by scissors. The first limiting component is disposed in the tube body, and two ends of the first limiting component are fixed at two ends of the tube body. A fixing component is disposed on the tube body with respect to the first limiting component, a fixing groove is disposed on the fixing component, the fixing groove is perforated, and the first fixing component penetrates through the fixing groove.

5 Claims, 4 Drawing Sheets

SURGERY DRAINAGE TUBE

TECHNICAL FIELD

The present disclosure relates to a technical field of surgery drainage tubes, in particular to a detachable surgery drainage tube capable of being sutured and fixed.

BACKGROUND

Anastomotic stoma fistula is the most common serious complication after gastrointestinal surgery (e.g., gastric, colorectal, and rectal cancer surgery) and one of the main causes of patient death. Taking colorectal cancer surgery as an example, according to statistics, incidence of the anastomotic stoma fistula after colorectal cancer surgery is as high as 3-6%, and a number of deaths caused by anastomotic complications accounts for about ⅓ of a total number of deaths after colorectal cancer surgery each year. The anastomotic stoma fistulas after colorectal resection often occur within 4-9 days after surgery, and in a few patients they can suffer around 10 days after surgery. Causes of the anastomotic stoma fistula are generally classified as poor anastomotic blood flow, excessive anastomotic tension, and poor bowel preparation. Patients having chronic wasting diseases such as diabetes mellitus, malnutrition, or long-term hormone use are also high in risk of the anastomotic stoma fistula.

Once the anastomotic stoma fistula occurs, the most important treatment is drainage and irrigation, and most anastomotic stoma fistulas can be cured by conservative treatment as long as there is reliable and unobstructed drainage. A surgery drainage tube is mostly placed around an anastomotic stoma during the surgery, but due to facts that a body position of postoperative patients is changed, intestinal swelling gas and intestinal peristalsis are caused, the surgery drainage tube is frequently displaced, so that a drainage effect of the surgery drainage tube is lost, and a protection effect of the surgery drainage tube on the anastomotic stoma is lost.

Therefore, a technical problem of the prior art is that the surgery drainage tube is displaced with respect to the anastomotic stoma.

SUMMARY

Embodiments of the present disclosure provide a detachable surgery drainage tube capable of being secured and fixed, solving a technical problem of the prior art that a surgery drainage tube is displaced with respect to an anastomotic stoma, so that a technical effect that a position of the surgery drainage tube is stable with respect to the anastomotic stoma is achieved.

The embodiments of the present disclosure provide a surgery drainage tube, including a tube body, a suture line, and a first limiting component. The tube body is hollow. The suture line has a length, and is configured to act on a part to be drained. The first limiting component is an annular structure, the first limiting component is inelastic, and a structure of the first limiting component is easy to be cut by scissors. The first limiting component is disposed in the tube body, and two ends of the first limiting component are fixed at two ends of the tube body. A part of the suture line is located on an outer side of the tube body and is configured to suture and fix the part to be drained. A fixing component is disposed in the tube body with respect to the first limiting component, a fixing groove is disposed on the fixing component, the fixing groove is perforated, and the first fixing component penetrates through the fixing groove. A through hole is disposed on the tube body, the suture line penetrates through at least one edge of the first limiting component through the through hole, and a position relationship between the suture line and the tube body is relatively fixed through the first limiting component.

Optionally, the fixing component is disposed in the tube body with respect to the first limiting component, the first limiting component and the fixing component are detachably connected, so that a connection relationship between the suture line and the tube body is removed.

Optionally, the first limiting component is a line body.

Optionally, the suture line is sleeved on the first limiting component, and the first limiting component is capable of being cut, so that a connection relationship between the suture line and the tube body is removed.

Optionally, the surgery drainage tube further includes a second limiting component. The second limiting component is disposed between the first limiting component and the suture line, and two ends of the second limiting component are respectively connected with the first limiting component and the suture line. The second limiting component is movably connected with the first limiting component.

Optionally, the second limiting component includes an annular structure, and the second limiting component is sleeved on the first limiting component through the annular structure of the second limiting component.

Optionally, a middle part of the suture line is connected with the second limiting component, and two ends of the suture line are in a free state.

One or more technical solutions of the embodiments of the present disclosure have at least one or more of the following technical effects.

1. In the embodiments of the present disclosure, with use of the surgery drainage tube capable of being secured and fixed developed by the present disclosure, the tube body is firmly fixed around the anastomotic stoma, or some key parts of a human body, such as a diaphragm angle, a small pelvis inlet, and the Douglas fossa of a pelvic floor. Once an anastomotic stoma fistula occurs, the surgery drainage tube may play a role of effective drainage and fixed-point irrigation. Doctors no longer need to worry about serious abdominal infection caused by the surgery drainage tube being too far away from a lesion, and life safety of patients may be greatly guaranteed.

2. In the embodiments of the present disclosure, the first limiting component is the annular structure and is inelastic, one end of the suture line is secured and fixed with the part to be drained, another end of the suture line penetrates through the first limiting component having the annular structure, so that the suture line is fixed on the first limiting component through the first limiting component and the suture line, and the position between the tube body and the anastomotic stoma is further relatively fixed through the first limiting component and the suture line. In addition, based on facts that the structure of the first limiting component is easy to be cut by scissors and the two ends of the first limiting component are fixed at the two ends of the tube body, the structure of the first limiting component may be damaged from an outer end of the tube body with respect to the human body, and the connection relationship between the first limiting component and the suture line is removed, so that the tube body and the suture line are separated, and the tube body is pulled out of the human body, and the technical problem of the prior art that the surgery drainage tube is displaced with respect to the anastomotic stoma is solved, so that a technical effect that a position of the surgery drainage tube is stable with respect to the anastomotic stoma is achieved.

3. In the embodiments of the present disclosure, when the first limiting component is a line body, the first limiting component needs to be in a tensioning state, so that a shape of the first limiting component is ensured to not be changed by the external force. Meanwhile, if the part to be drained is displaced, the suture line pulls the first limiting component, due to a fact that the shape of the first limiting component may not be changed by the external force, the first limiting component pulls the tube body to further pull the tube body to move along with the part to be drained, so that a problem that the suture line pulls the first limiting component but cannot drive the tube body due to loosening of the first limiting component is avoided.

4. In the embodiments of the present disclosure, the first limiting component is detachably connected with the fixing component, or the first limiting component is designed as a separable body, so that the first limiting component may be pulled out of the tube body alone, thereby causing the suture line to lose an attached main body, and the suture line may be out of a limitation of the first limiting component, so that the tube body is separated from the suture line.

5. In the embodiments of the present disclosure, a fixing groove is disposed on the fixing component, the fixing groove is perforated, and the first fixing component penetrates through the fixing groove, so that one end of the first limiting component is fixed at the fixing groove. In this way, after the first limiting component having the annular structure is cut off, the first limiting component is pulled to enable the first limiting component and the fixing component to be smoothly disconnected, so that the first limiting component is completely and conveniently pulled out of the tube body. When the tube body is pulled away from the human body, if there is still a part of the first limiting component in the tube body, the part of the first limiting component is easy to be pulled out of the through hole of the tube body through the suture line, thereby affecting tissues of the human body and the suture line and the part of the first limiting component are easily blocked at the through hole to affect a pulling away of the tube body. The two problems may be avoided in the way above.

6. In the embodiments of the present disclosure, the first limiting component is the line body capable of being cut, so that an operator may cut the first limiting component in an outer of the tube body to change the first limiting component from the tensioning state to a relaxed state, and when the first limiting component is pulled out of the tube body alone, the suture line may be detached from the first limiting component where the first limiting component is cut off, to reach a releasable connection between the suture line and the first limiting component.

7. In the embodiments of the present disclosure, the second limiting component is additionally disposed to make an additional connection component between the suture line and the first limiting component. In this way, the suture line is completely outside the tube body to achieve complete exposure of the suture line to a field of views, which facilitates an overall control of the suture line during suturing; the first limiting component is more smoothly separated from the suture line, such as by setting the second limiting component in the annular shape to ensure that the second limiting component is conveniently separated from the first limiting component; and the suture line may easily penetrate through the second limiting component having the annular shape to facilitate a surgery operation.

Reference number: 1. part to be drained; 11. anastomotic stoma; 2. tube body; 21. through hole; 3. first limiting component; 4. fixing component; 41. fixing groove; 5. suture line; and 6. second limiting component.

DETAILED DESCRIPTION

The present disclosure provides a detachable surgery drainage tube capable of being secured and fixed, with use of the surgery drainage tube capable of being secured and fixed developed by the present disclosure, a tube body 2 is firmly fixed around the anastomotic stoma 11, or some key parts of a human body, such as a diaphragm angle, a small pelvis inlet, and the Douglas fossa of a pelvic floor. Once an anastomotic stoma 11 fistula occurs, the surgery drainage tube may play a role of effective drainage and fixed-point irrigation. Doctors no longer need to worry about serious abdominal infection caused by the surgery drainage tube being too far away from a lesion, and life safety of patients may be greatly guaranteed.

Figure 1:
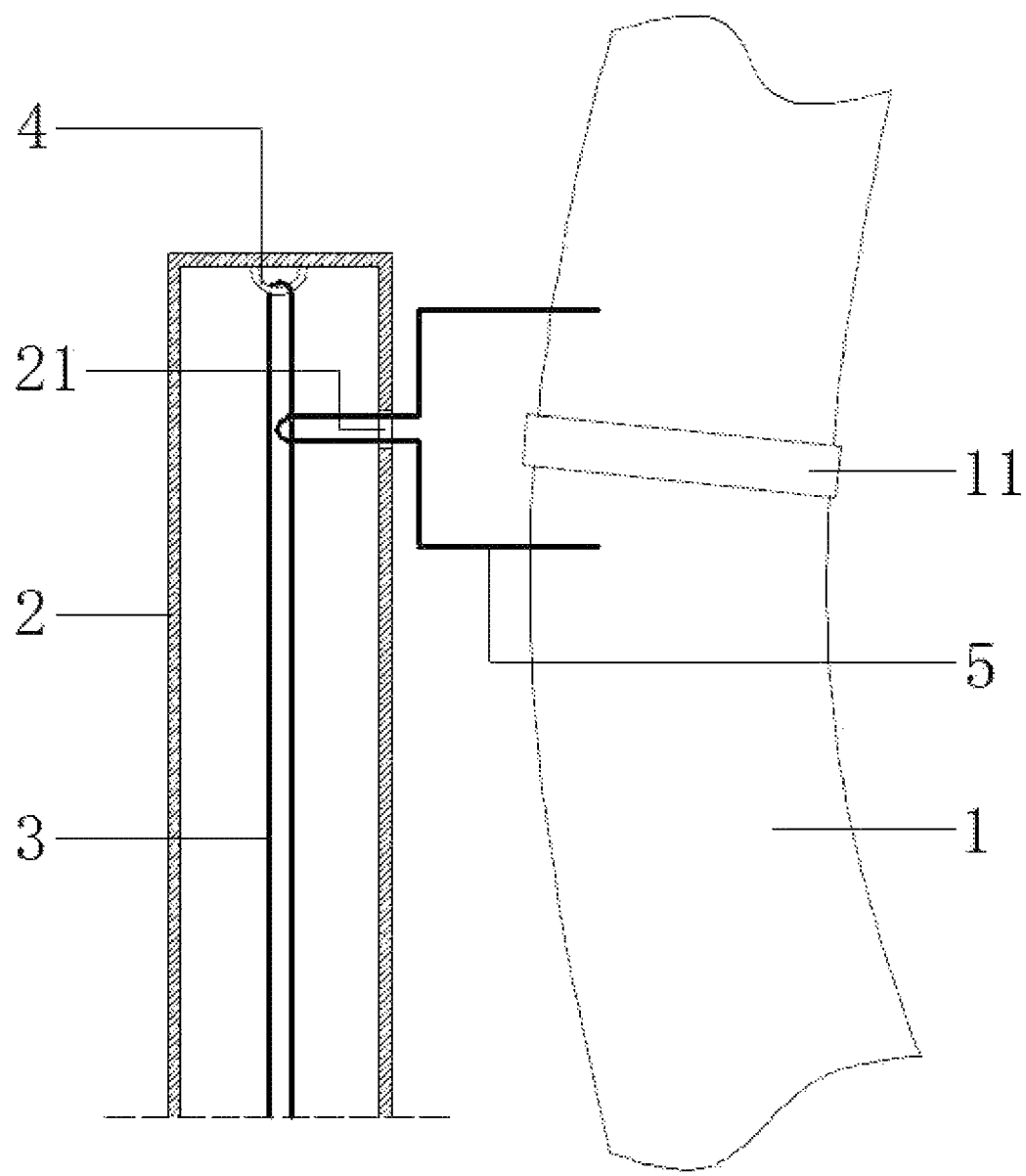
FIG. 1 is a front cross-sectional structural schematic diagram of a surgery drainage tube according to one embodiment of the present disclosure.

The present disclosure provides a detachable surgery drainage tube capable of being secured and fixed, as shown in FIG. 1, the surgery drainage tube acts on an anastomotic stoma 11 of a part to be drained in a human body, and the surgery drainage tube includes a tube body 2, a fixing component 4, a first limiting component 3, and a suture line 5. The tube body 2 is hollow, a through hole 21 is disposed on the tube body 2 with respect to the anastomotic stoma 11. The fixing component 4 is disposed on the tube body 2, the first limiting component 3 is fixed in the tube body 2 through the fixing component 4, and the first limiting component 3 is connected with the part to be drained through the suture line 5, so that a position of the surgery drainage tube is stable with respect to the anastomotic stoma 11. In addition, the first limiting component 3 is an annular structure, the suture line 5 penetrates through at least one edge of the first limiting component 3, and a position relationship between the suture line 5 and the tube body 2 is relatively fixed through the first limiting component 3.

Figure 4:
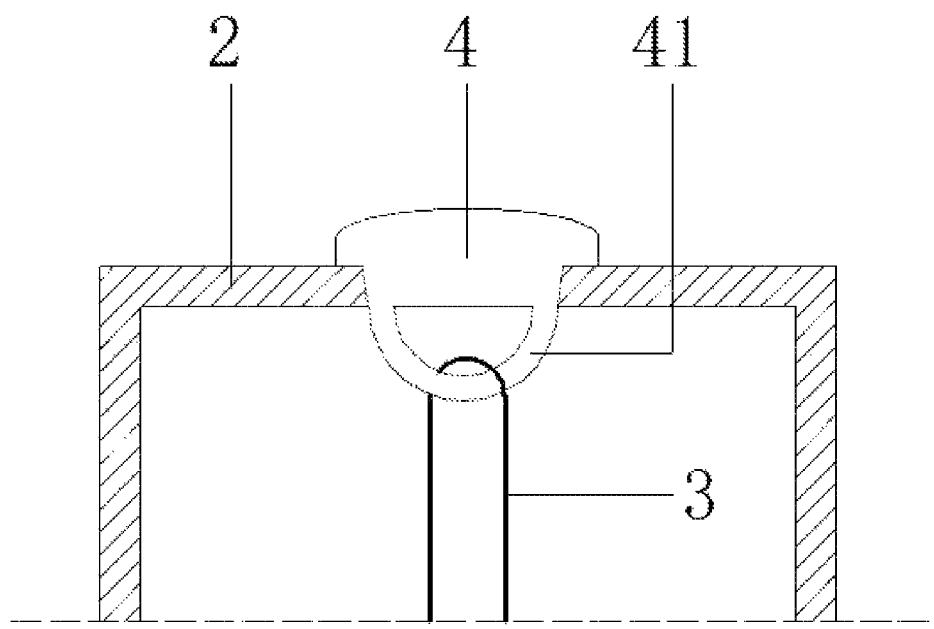
FIG. 4 is a partial cross-sectional structural schematic diagram of the surgery drainage tube according to the one embodiment of the present disclosure.

Furthermore, the tube body 2 is a conventional style of surgery drainage tubes having one or more drainage holes. It should be noted that the through hole 21 in the tube body 2 may also be instead by a drainage hole. It will be appreciated that the fixing component 4 and the tube body 2 may be integral and may also be a combination. In one example, as shown in FIG. 4, the fixing component 4 and the tube body 2 are two parts, the fixing component 4 is fixed at a bottom of the tube body 2, and a fixing groove 41 is disposed on the fixing component 4, so that the first limiting component 3 conveniently penetrates through and connects with the fixing component 4. In this way, the first limiting component 3 is completely pulled out of the tube body 2 after a structure of the first limiting component 3 is damaged, and the first limiting component 3 is prevented from being clamped on the fixing component 4. In another example, the first limiting component 3 and the fixing component 4 are detachably connected such that a connection relationship between the suture line 5 and the tube body 2 is removed.

Furthermore, the first limiting component 3 is disposed in the tube body 2, two ends of the first limiting component 3 are fixed at two ends of the tube body 2. The first limiting component 3 has two types, a first type is that the first limiting component 3 is detachably connected with the fixing component 4, and a second type is that the first limiting component 3 is separable. The first limiting component 3 is inelastic, and the structure of the first limiting component 3 is easy to be cut by scissors, such as may be cut, broken, or blown, so that the connection relationship between the suture line 5 and the tube body 2 is removed, and the first limiting component 3 loses ability of limiting the suture line 5 or the second limiting component 6 through damaging the structure of the first limiting component 3. It should be noted that the tube body 2 has a certain length that may extend from the body to the outside of the body, the first limiting component 3 also has a certain length that may extend out of the body from the body, and the first limiting component 3 is in a state which may be operated by an operator, for example, the length of the first limiting component 3 being greater than or equal to bi-length of the tube body 2, so that the first limiting component 3 extends out of the tube body 2. In one example, the first limiting component 3 is specifically a line body or a rod body, and the first limiting component 3 is stable in shape in the tube body 2, such as an absorbable surgical suture line, the first limiting component 3 is in a tensioning state in the tube body 2, the line body is in a tensioning state so as to ensure that a free length of the suture line 5 can only move in a small range, thereby the surgery drainage tube is avoided from being displaced with respect to the anastomotic stoma 11.

In addition, the first limiting component 3 is movably connected with the suture line 5, when the suture line 5 is not limited by the first limiting component 3, the first limiting component 3 is pulled to separate out the suture line 5 from the first limiting component 3. It should be noted that when the first limiting component 3 is in a form of a single line body, when the first limiting component 3 is cut off and pulled outward, there is a probability that the first limiting component 3 is pulled out from a coil formed by threading of the suture line 5, there is also a problem that the coil formed by threading of the first limiting component 3 and the suture line 5 may interfere and mingle, thereby causing the first limiting component 3 cannot be smoothly separated with the suture line 5. However, when the first limiting component 3 is bent to form an annular structure, the annular structure on the first limiting component 3 is disposed on the fixing component 4 in a penetrating mode, and the suture line 5 is disposed around the first limiting component 3 in a penetrating mode through the annular structure on the first limiting component 3. In this connection state, one side of the annular structure of the first limiting component 3 is cut off, and the whole first limiting component 3 can be pulled out from the cut-off position, so that the coiled formed by threading of the first limiting component 3 and the suture line 5 is smoothly separated and the tube body 2 is smoothly pulled out of the human body.

Furthermore, the suture line 5 may be absorbed in the human body, the suture line 5 has a certain length, and a part of the suture line 5 is disposed the outer side of the tube body 2 and is configured to suture and fix the part 1 to be drained.

In one example, the second limiting component 6 may also be added such that connection and separation between the first limiting component 3 and the suture line 5 is smoother. It should be noted that the suture line 5 may be set as one or more, and the suture line 5 is set in a form of a first end connected with the first limiting component 3 or the second limiting component 6 and a second end configured to be sutured on the part 1 to be drained. And there is also another form to set the suture line 5 that a middle part of the suture line 5 is connected with the first limiting component 3 or the second limiting component 6, and two ends of the suture line 5 are in a free state so as to respectively connected with two side of the anastomotic stoma 11.

Figure 2:
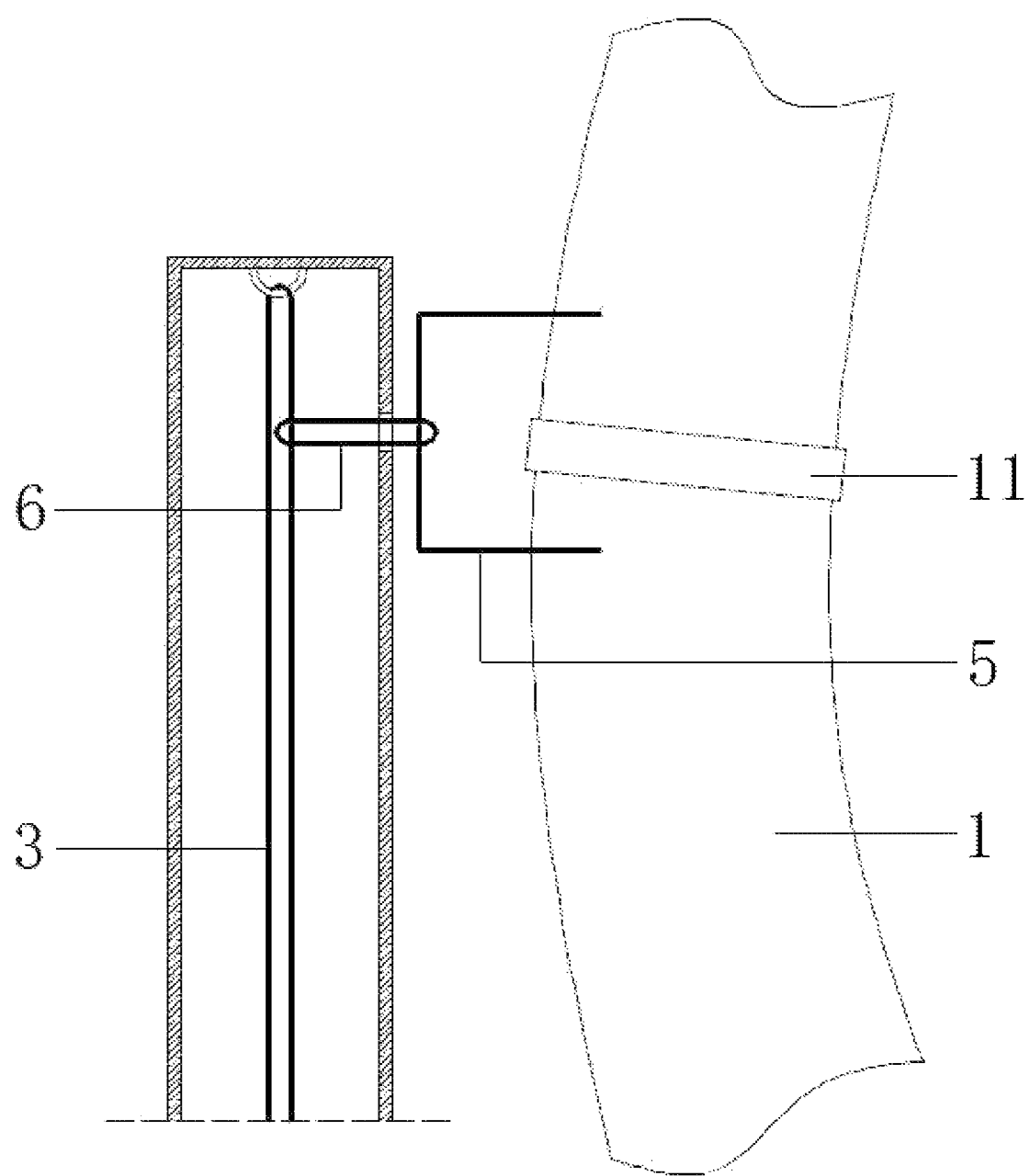
FIG. 2 is a front cross-sectional structural schematic diagram of the surgery drainage tube according to another embodiment of the present disclosure.
Figure 3:
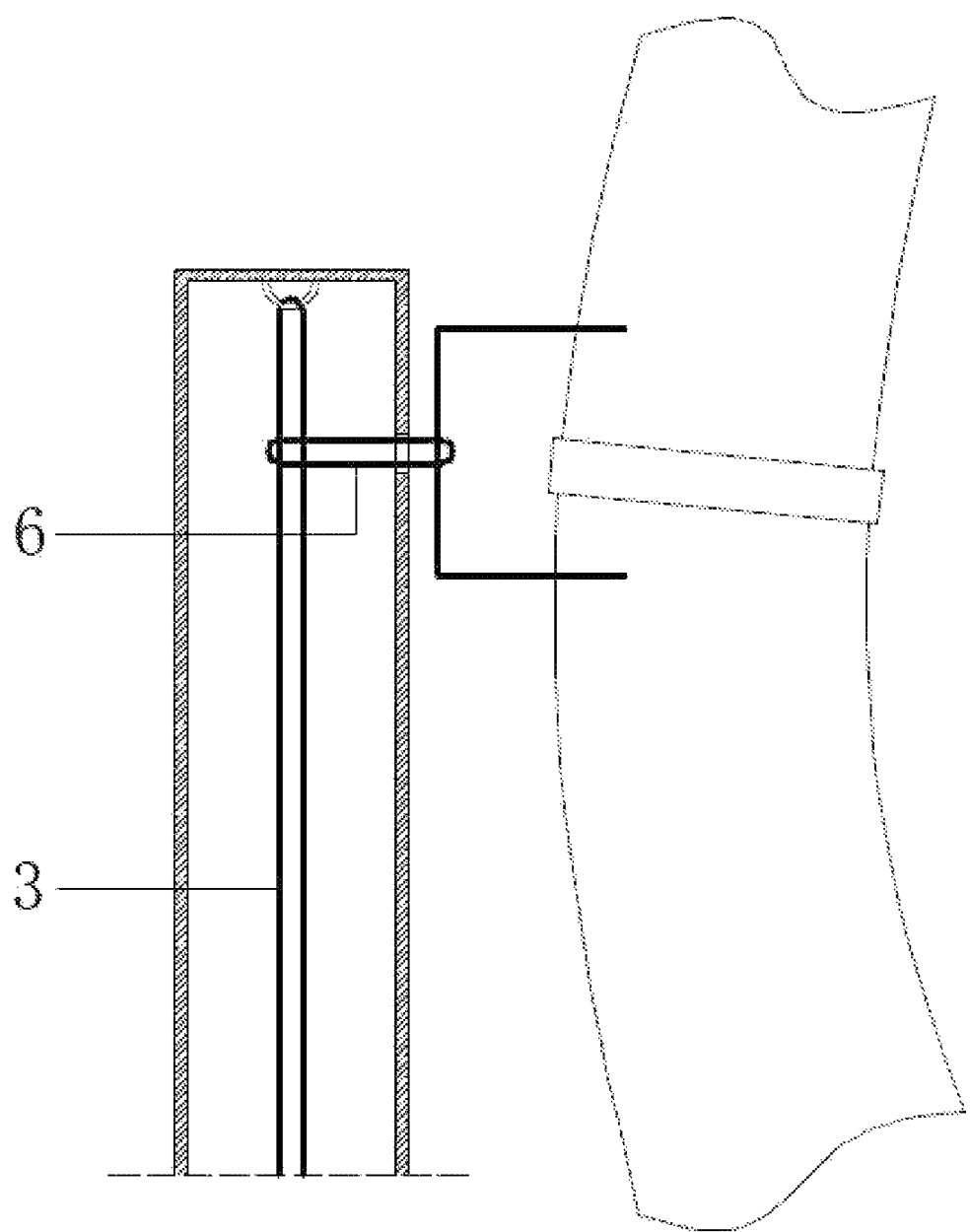
FIG. 3 is a front cross-sectional structural schematic diagram of the surgery drainage tube according to another embodiment of the present disclosure.

Furthermore, as shown in FIGS. 2-3, the second limiting component 6 is disposed between the first limiting component 3 and the suture line 5, and two ends of the second limiting component 6 are respectively connected with the first limiting component 3 and the suture line 5. The second limiting component 6 is movably connected with the first limiting component 3, a specific connection mode may be that the second limiting component 6 penetrates through one edge of the first limiting component 3 or the second limiting component 6 penetrates through both sides of the first limiting component 3. In order to ensure that the second limiting component 6 is secure within the human body, the second limiting component 6 is specifically the absorbable surgical suture line. In one example, the second limiting component 6 includes an annular structure, and the second limiting component 6 is sleeved on the first limiting component 3 through the annular structure of the second limiting component 6. It should be noted that preferably the through hole 21 of the tube body 2 is penetrated by the second limiting member 6 to avoid friction between the suture line 5 and the through hole 21, thereby ensuring a structural strength of the suture line 5.

A working principle of the present disclosure is as follows.

Firstly, the tube body 2, the first limiting component 3, and the suture line 5 are combined into a whole (another example further includes the second limiting component 6), then the whole body is placed near the anastomotic stoma 11, and the tube body 2 and the part 1 to be drained are sutured and fixed together by using the suture line 5. When the tube body 2 needs to be removed, the first limiting component 3 is disconnected from the tube body 2 through disconnecting the first limiting component 3 and the tube body 2, for example, the first limiting component 3 is cut off at the bottom of a guide tube, and the first limiting component 3 is pulled out of the guide tube, so that the connection relationship between the first limiting component 3 and the suture line 5 is invalid, the connection relationship between the tube body 2 and the suture line 5 is invalid, and the tube body 2 may be conveniently pulled out of the human body, the suture line 5 is the absorbable surgical suture line, and the suture line 5 may be naturally absorbed in the human body.

Technical effects of the present disclosure are as follows.

1. In the embodiments of the present disclosure, the first limiting component is the annular structure and is inelastic, one end of the suture line is secured and fixed with the part to be drained, another end of the suture line penetrates through the first limiting component having the annular structure, so that the suture line is fixed on the first limiting component through the first limiting component and the suture line, and the position between the tube body and the anastomotic stoma is further relatively fixed through the first limiting component and the suture line. In addition, based on facts that the structure of the first limiting component is easy to be cut by scissors and the two ends of the first limiting component are fixed at the two ends of the tube body, the structure of the first limiting component may be damaged from an outer end of the tube body with respect to the human body, and the connection relationship between the first limiting component and the suture line is removed, so that the tube body and the suture line are separated, and the tube body is pulled out of the human body, and the technical problem of the prior art that the surgery drainage tube is displaced with respect to the anastomotic stoma is solved, so that a technical effect that a position of the surgery drainage tube is stable with respect to the anastomotic stoma is achieved.

2. In the embodiments of the present disclosure, when the first limiting component is a line body, the first limiting component needs to be in a tensioning state, so that a shape of the first limiting component is ensured to not be changed by the external force. Meanwhile, if the part to be drained is displaced, the suture line pulls the first limiting component, due to a fact that the shape of the first limiting component may not be changed by the external force, the first limiting component pulls the tube body to further pull the tube body to move along with the part to be drained, so that a problem that the suture line pulls the first limiting component but cannot drive the tube body due to loosening of the first limiting component is avoided.

3. In the embodiments of the present disclosure, the first limiting component is detachably connected with the fixing component, or the first limiting component is designed as a separable body, so that the first limiting component may be pulled out of the tube body alone, thereby causing the suture line to lose an attached main body, and the suture line may be out of a limitation of the first limiting component, so that the tube body is separated from the suture line.

4. In the embodiments of the present disclosure, a fixing groove is disposed on the fixing component, the fixing groove is perforated, and the first fixing component penetrates through the fixing groove, so that one end of the first limiting component is fixed at the fixing groove. In this way, after the first limiting component having the annular structure is cut off, the first limiting component is pulled to enable the first limiting component and the fixing component to be smoothly disconnected, so that the first limiting component is completely and conveniently pulled out of the tube body. When the tube body is pulled away from the human body, if there is still a part of the first limiting component in the tube body, the part of the first limiting component is easy to be pulled out of the through hole of the tube body through the suture line, thereby affecting tissues of the human body and the suture line and the part of the first limiting component are easily blocked at the through hole to affect a pulling away of the tube body are avoided. The two problems may be avoided in the way above.

5. In the embodiments of the present disclosure, the first limiting component is the line body capable of being cut, so that an operator may cut the first limiting component in an outer of the tube body to change the first limiting component from the tensioning state to a relaxed state, and when the first limiting component is pulled out of the tube body alone, the suture line may be detached from the first limiting component where the first limiting component is cut off, to reach a releasable connection between the suture line and the first limiting component.

6. In the embodiments of the present disclosure, the second limiting component is additionally disposed to make an additional connection component between the suture line and the first limiting component. In this way, the suture line is completely outside the tube body to achieve complete exposure of the suture line to a field of views, which facilitates an overall control of the suture line during suturing; the first limiting component is more smoothly separated from the suture line, such as by setting the second limiting component in the annular shape to ensure that the second limiting component is conveniently separated from the first limiting component; and the suture line may easily penetrate through the second limiting component having the annular shape to facilitate a surgery operation.

What is claimed is:

1. A surgery drainage tube, comprising:
    a tube body;
    a suture line; and
    a first limiting component;
    wherein the tube body is hollow; the suture line has a length, and is configured to act on a part to be drained; the first limiting component is a line body and is an annular structure, the first limiting component is inelastic; the first limiting component is disposed in the tube body, and two ends of the first limiting component are fixed at two ends of the tube body; a part of the suture line is located on an outer side of the tube body and is configured to be sutured and fixed to the part to be drained;
    wherein a fixing component is disposed in the tube body with respect to the first component, a fixing groove is disposed on the fixing component, the fixing groove is perforated, and the first limiting component penetrates through the fixing groove; a through hole is disposed on the tube body, the suture line penetrates through at least one edge of the first limiting component through the through hole;
    wherein the suture line is sleeved on the first limiting component, and the first limiting component is capable of being cut, so that a connection relationship between the suture line and the tube body is removed.

2. The surgery drainage tuba according to claim 1, wherein the first limiting component and the fixing component are detachably connected, so that a connection relationship between the suture line and the tube body is removed.

3. The surgery drainage tube according to claim 1, further comprising;
    a second limiting component;
    wherein the second limiting component is disposed between the first limiting component and the suture line, and two ends of the second limiting component are respectively connected with the first limiting component and the suture line; and the second limiting component is movably connected with the first limiting component.

4. The surgery drainage tube according to claim 3, wherein the second limiting component comprises an annular structure, and the second limiting component is sleeved on the first limiting component through the annular structure of the second limiting component.

5. The surgery drainage tube according to claim 4, wherein a middle part of the suture line is connected with the second limiting component, and two ends of the suture line are in a free state.

* * * * *